United States Patent [19]

Manghisi et al.

[11] 4,061,637

[45] Dec. 6, 1977

[54] CERTAIN 4-ARYL-5-(4-PHENYLPIPERAZINO)ALKYL-4-THIAZOLIN-2-ONES

[75] Inventors: Elso Manghisi, Monza; Giuseppe Cascio; Giancarlo Fregnan, both of Milan, all of Italy

[73] Assignee: Istituto Luso Farmaco d'Italia S.r.l., Milan, Italy

[21] Appl. No.: 576,582

[22] Filed: May 12, 1975

[30] Foreign Application Priority Data

May 14, 1974 Italy .................................. 22693/74
Apr. 18, 1975 Italy .................................. 22521/75

[51] Int. Cl.$^2$ .......................................... C07D 417/06

[52] U.S. Cl. .............................. 260/268 PH; 544/58; 544/133; 260/256.5 R; 260/268 BC; 260/268 FT; 260/268 H; 260/293.66; 260/293.68; 260/295 S; 260/295.5 S; 260/299; 260/306.7 R; 260/454; 260/250 R; 424/245; 424/246; 424/250; 424/251; 424/267; 424/270; 424/248.51

[58] Field of Search ............... 260/306.7 R, 268 H, 260/247.1 M, 293.68, 268 PH

[56] References Cited

U.S. PATENT DOCUMENTS 2,921,936  1/1960  de Stevens .................. 260/306.7 R Primary Examiner—R. Gallagher
Attorney, Agent, or Firm—Flynn & Frishauf

[57] ABSTRACT

The invention provides novel 4-aryl-5-aminoalkyl-4-thiazolin-2-ones and their salts and complexes which have activity on the central nervous system, the cardiovascular system, and anti-inflammatory, adrenolytic and anti-ulcer activity.

9 Claims, No Drawings

CERTAIN 4-ARYL-5-(4-PHENYLPIPERAZINO)ALKYL-4-THIAZOLIN-2-ONES

This invention provides the compounds of the formula:

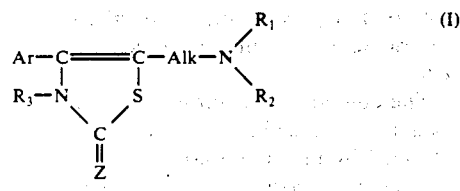

and their pharmaceutically acceptable salts and complexes, in which Ar represents a substituted or unsubstituted mono-or polycarbocyclic aryl group, such as phenyl or substituted phenyl, which may have one or more identical or different substituents, e.g. lower alkyl, for example methyl, ethyl, n-propyl or isopropyl, trifluoromethyl, lower alkoxy, for example methoxy, ethoxy, n-propyloxy, isopropyloxy or n-butyloxy, lower alkenyloxy, for example vinyloxy or allyloxy, lower alkylenedioxy, for example methylenedioxy, halogen, for example fluoro, chloro or bromo, alkylmercapto, for example methylmercapto, or ethylmercapto, nitro, amino or substituted amino, such as lower N,N-dialkylamino, for example N,N-dimethylamino or N,N-diethylamino, or the carboxylic aryl radical may be a bicyclic radical such as naphthyl, e.g. 1-naphthyl or 2-naphthyl, or naphthyl substituted with one or more identical or different substituents, for example alkylnaphthyl, trifluoromethylnaphthyl, alkoxynaphthyl, alkenyloxynaphthyl, halogenonaphthyl or aminonaphthyl; Alk represents a saturated or unsaturated linear or branched carbon atom chain comprising 1 to 3 carbon atoms;

is a mono- or di-substituted amino group, in which the substituents may be lower alkyl, carbocyclic monocyclic aryl, particularly phenyl, monocarbocyclic lower arylalkyl, particularly phenylalkyl; Z is an atom of oxygen or sulphur; and $R_3$ represents a hydrogen atom or a linear or branched lower alkyl, for example methyl, ethyl, propyl, or isopropyl, or a free or etherified lower hydroxyalkyl, for example 2-hydroxyethyl, 3-hydroxypropyl, 2-methoxyethyl, 3-methoxypropyl, or 2'-hydroxyethoxyethyl, arylalkyl, for example benzyl, dialkylaminoalkyl, for example N,N-diethylaminoethyl, or lower aliphatic acyl, for example acetyl, propionyl, carbamoyl, N-alkylcarbamoyl, N-phenylcarbamoyl, N-alkylthiocarbamoyl, N-phenylthiocarbamoyl etc., or aromatic acyl, substituted or otherwise by halogen or methoxy, for example benzoyl, p-chlorobenzoyl, p-methoxybenzoyl or 3,4,5-trimethoxybenzoyl.

The N-monosubstituted amino group -NR₁R₂ may be N-alkylamino, for example methylamino, ethylamino, propylamino or isopropylamino, N-cycloalkylamino, for example N-cyclohexylamino, N-hydroxyalkylamino, for example N-2-hydroxyethylamino, N-arylalkylamino, for example benzylamino, phenylethylamino or 3,4-dimethoxyphenylethylamino, N-aryloxyalkylamino, for example phenoxy-isopropylamino, N-dialkylaminoethylamino, for example N',N'-diethylaminoethylamino or N-arylamino, for example N-phenylamino or substituted N-phenylamino.

The N,N-disubstituted amino group $-NR_1R_2$ may be N,N-dialkylamino, for example N,N-dimethylamino, N-methyl-N-ethylamino, N,N-diethylamino, N,N-di-n-propylamino, N,N-di-iso-propylamino or N-methyl-diethylaminoethylamino or N-cycloalkyl-N-alkylamino in which the cycloalkyl has 3 to 8 carbon atoms, for example N-cyclopentyl-N-methylamino or N-cyclohexyl-N-ethylamino, N-lower alkyl-N-phenylalkylamino, for example N-benzyl-N-methylamino, N-ethyl-N-phenylethylamino or N-methyl-N-phenylethylamino, or any other disubstituted amino group such as N-hydroxyalkyl-N-alkylamino in which the hydroxyl is separated from the nitrogen by at least two carbon atoms, for example N-ethyl-N-(2-hydroxyethyl)-amino, or N,N-dihydroxyalkylamino, for example N,N-di(2-hydroxyethyl)-amino.

The radical

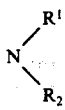

may also be a N,N-alkyleneimino group in which the alkylene has 3 to 8 carbon atoms, for example 1-pyrrolidino, 1-piperidino, 1-[4-(p-chlorophenyl)-1,2,3,6-tetrahydropyridino], 2-methyl-1-piperidino, 4-hydroxy-4-phenyl-1-piperidino, 4-hydroxy-4-p-chlorophenyl-1-piperidino, 7,12-dioxa-3-azaspiro-[5,6]-dodec-3-yl, 4-carboxamino-4-phenyl-1-piperidino, 4-benzoylamino-1-piperidino or 4-p-fluorobenzoyl-1-piperidino, 1-N,N-(1,6-hexylene)-imino, or 1-N-N-(1,7-heptylene)-imino, N,N-oxo-alkyleneimino in which the alkylene has preferably 4 carbon atoms, for example 4-morpholino, N,N-thio-alkyleneimino, in which the alkylene has preferably 4 carbon atoms, for example 4-thio-morpholino, or N,N-azaalkylene-imino in which the alkylene has 4 to 6 carbon atoms or in which the "aza" nitrogen may be substituted for example by lower alkyl, for example methyl, ethyl, or propyl, lower hydroxyalkyl, for example hydroxyethyl, lower alkoxyalkyl, for example methoxyethyl, lower alkanoyloxyalkyl, for example acetoxyethyl, lower arylalkyl, for example benzyl, diphenylmethyl, 2-phenylethyl, 2-3'-indolylethyl, or by monocarbocyclic aryl, preferably phenyl, substituted or unsubstituted by halogen or alkyl, lower alkoxy or nitro, for example phenyl, 2-tolyl, 2,3-xylyl, 4-chlorophenyl, or 2-methoxyphenyl, or finally by a monocarbocyclic heterocyclic aryl, for example 2-pyridine, 2-furan, 2-thiophene, 2-pyrimidine, such as piperazino, 4-methyl-1-piperazino, 4-ethyl-1-piperazino, 4-(2-hydroxyethyl)-1-piperazino, 4-(2-acetoxyethyl)-1-piperazino, 4-benzyl-1-piperazino, 4-[2'-(3'-indolyl)-ethyl]-1-piperazino, 4-phenyl-1-piperazino, 4-p-chlorophenyl-1-piperazino, 4-2'-methoxyphenyl-1-piperazino, 4-2'-pyridyl-1-piperazino, 4-3'-pyridyl-1-piperazino, or 4-(2'-pyrimidyl)-1-piperazino etc.

Preferably, in the compounds of formula I Ar is phenyl, p-fluorophenyl, p-chlorophenyl or p-methoxyphenyl, Alk is CH₂ or CH₂CH₂, NR₁R₂ is diethylamino, N'-phenylpiperazino, morpholino, piperidino, 4'-hydroxy-4'-p-chlorophenylpiperidino, N-methylphenylethylamino, N'-o-methoxyphenylpiperazino, 4'- benzoylaminopiperidino, 7,12-dioxa-3-azaspiro[5,6]dodec-3-yl, dimethylamino, isopropylamino, phenylethylamino, 3′,4′-dimethoxyphenylethylamino, or phenoxyisopropylamino, Z is oxygen or sulphur, and R₃ is hydrogen, methyl, acetyl, methylaminocarbonyl, or benzoyl.

According to a feature of the invention, the compounds of formula I may be prepared by reacting a compound of the formula:

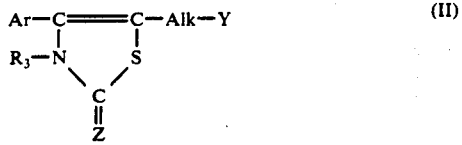  (II)

in which Ar, R₃, Z have the meanings given above, Alk is alkylene of 2 of 3 carbon atoms and Y is a halogen atom, with an amine of formula

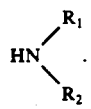

The compounds of formula (I) in which R₃ is other than hydrogen may also be obtained from compounds of formula (I) in which R₃ is hydrogen, by alkylation or acylation, optionally after preparing the sodium salt, by reaction with compounds of general formula R₃X in which R₃ has the meanings given heretofore and X represents a halogen atom or a tosyl radical, or the aryl residue of an anhydride. The alkylating agent used may be an alkylene oxide, for example ethylene oxide or propylene oxide, and the acylation agent may be an isocyanate of formula R₄NCO in which R₄ represents a lower alkyl group, for example methyl, ethyl, propyl, butyl, or monocarbocyclic aryl, for example phenyl, or a corresponding isothiocyanate of formula R₄NCS.

The compounds of formula I may also be obtained from compounds of the formula:

  (V)

in which Ar and Z have the meanings given heretofore, by Mannich condensation with an aldehyde and the appropriate amine.

The intermediates of formula II, in which R₃ represents a hydrogen atom and Z is an oxygen atom, may be obtained by reacting a compound of the formula:

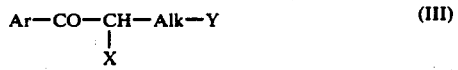  (III)

in which X and Y represent halogen atoms and Ar and Alk have the meanings given above with ammonium thiocarbamate

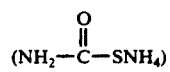

in an alcoholic environment under hot conditions, or with an alkali metal thiocyanate in an aqueous alcoholic medium under hot conditions; in the latter case the compounds of formula (IV) are formed as intermediates.

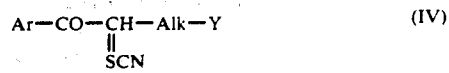  (IV)

which give products of formula II by treatment under hot conditions with organic or inorganic acids (hydrochloric acid, or a mixture of acetic acid and sulphuric acid).

The compounds of formula (II) in which R₃ is other than hydrogen and Z represents an oxygen atom may be obtained by reacting a compound of the formula (III) with an ethyl N-substituted thiocarbamate of formula

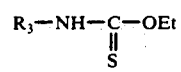

in dioxan under hot conditions.

Compounds of formula (II) in which R₃ is a hydrogen atom and Z a sulphur atom may be obtained from compounds of formula (III) by reacting them with ammonium dithiocarbamate under hot conditions in an alcoholic environment.

Compounds of formula (II) in which R₃ is other than hydrogen and Z is a sulphur atom may be obtained by reacting compounds of general formula (III) with N-monosubstituted dithiocarbamic acid under hot conditions in an alcoholic environment; in this case the substances of formula (VI) are formed as intermediates:

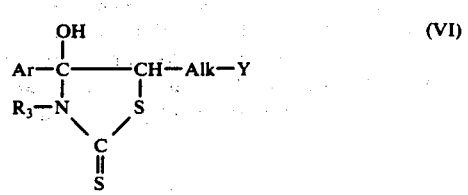  (VI)

and give compounds of formula II by treatment under hot conditions with organic or inorganic acids (hydrochloric acid, or a mixture of acetic acid and sulphuric acid).

Compounds of formula (II) in which R₃ is other than a hydrogen atom may also be obtained from the compounds of formula II in which R₃ represents a hydrogen atom, by alkylation or acylation, possibly after preparing the sodium salt, with compounds of general formula R₃X in which R₃ and X have the meanings given above, or by alkylation with alkylene oxides or acylation with R₄NCO isocyanates or R₄NCS isothiocyanates in which R₄ has the meaning given above.

Compounds of formula (V) are obtained from compounds of formula Ar—CO—CH₂—X, in which X represents a halogen atom and Ar has the meanings given above, using the methods already described for synthesis of compounds of formula (II).

For the synthesis of compounds of formula (III) reference should be made to the methods given in Italian patent Application No. 23444 A/72 filed Apr. 22, 1972 which corresponds in part to U.S. patent application Ser. No. 352,346, filed Apr. 18, 1973 (now U.S. Pat. No. 3,951,978).

Salts of compounds of formula (I) may be prepared with pharmaceutically acceptable inorganic acids, such as hydrochloric, hydrobromic, nitric, sulphuric, or phosphoric acid, and with organic carboxylic acids such as acetic, propionic, glycolic, malonic, succinic, maleic, hydroxymaleic, fumaric, malic, tartaric, citric, glucaronic, benzoic, mandelic, salicylic, 4-aminosalicylic, 2-phenoxybenzoic, 2-acetoxybenzoic, pamoic, nicotinic or isonicotinic acid, or with organic sulphonic acids such as methanesulphonic, ethanesulphonic, 2-hydroxyethanesulphonic, ethane-1,2-disulphonic, p-toluene-sulphonic, or naphthalene-2-sulphonic acid. Mono or poly salts are formed according to the salifiable groups present in the molecule. Salts and complexes of compounds of general formula (I) may be prepared with alkali metals such as sodium and potassium, or heavy metals such as copper and zinc.

The compounds of formula I and their pharmaceutically acceptable salts and complexes have considerable activity on the central nervous system and the cardiovascular system, and anti-inflammatory, adrenolytic and anti-ulcer activity.

They may be administered orally, by injection or through the rectum in the form of suitable pharmaceutical formulations in solid, liquid or suspension form (e.g. as tablets, capsules, phials, syrups or suppositories).

The Tables given below summarise certain pharmacological characteristics of various compounds of the present invention, the symbols of which have the following meanings:

LR 599 : 4-p-fluorophenyl-5-$\beta$-(N'-phenylpiperazino)ethyl-4-thiazolin-2-one LR 602 : 4-p-fluorophenyl-5-$\beta$-diethylaminoethyl-4-thiazolin-2-one LR 613 : 4-p-fluorophenyl-5-$\beta$-[(4'-hydroxy-4'-p-chlorophenyl)-piperidino]-ethyl-4-thiazolin-2-one hydrochloride LR 616 - 4-p-fluorophenyl-5-$\beta$-(N-methylphenylethylamino)ethyl-4-thiazolin-2-one maleate LR 617 : 4-p-fluorophenyl-5-$\beta$-piperidinoethyl-4-thiazolin-2-one hydrochloride LR 618 : 4-p-fluorophenyl-5-$\beta$-morpholinoethyl-4-thiazolin-2-one hydrochloride LR 620 : 4-p-methoxyphenyl-5-$\beta$-(N-methylphenylethylamino)-ethyl-4-thiazolin-2-one maleate LR 628 : 4-p-chlorophenyl-5-$\beta$-(N-methylphenylethylamino)ethyl-4-thiazolin-2-one maleate LR 630 : 4-phenyl-5-$\beta$-(N-methylphenylethylamino)ethyl-4-thiazolin-2-one maleate LR 637 : 4-phenyl-5-$\beta$-(N'-phenylpiperazino)ethyl-4-thiazolin-2-one LR 638 : 4-p-chlorophenyl-5-$\beta$-(N'-phenylpiperazino)ethyl-4-thiazolin-2-one LR 639 : 4-p-methoxyphenyl-5-$\beta$-(N'-phenylpiperazino)ethyl-4-thiazolin-2-one LR 648 : 4-p-fluorophenyl-5-$\beta$-[7,12-dioxa-3-azaspiro[5,6]-dodec-3-yl]-ethyl-4-thiazolin-2-one hydrochloride LR 652 : 3-methyl-4-p-fluorophenyl-5-$\beta$-(N'-phenylpiperazino)-ethyl-4-thiazolin-2-one LR 653 : 3-acetyl-4-p-fluorophenyl-5-$\beta$-(N'-phenylpiperazino)- ethyl-4-thiazolin-2-one LR 659 : 4-p-chlorophenyl-5-piperidinomethyl-4-thiazolin-2-one LR 660 : 4-p-chlorophenyl-5-(N'-phenylpiperazino)-methyl-4-thiazolin-2-one

PHARMACOLOGICAL METHODS

Fibrillation induced by $CaCl_2$ of the rat anaesthetised with urethane (1 g/kg ip)

The method described by Malinow and colleagues (Rev. Argent. Cardiol., 19, 120, 1952) was followed, which consists of inducing cardiac fibrillation by administering intravenously 2 ml/kg of an 8% solution of $CaCl_2$ in rats pretreated intravenously with scalar doses of anti-arrhythmics. The $ED_{50}$ was calculated for each active drug.

Arrhythmias induced by electrical stimulation of the isolated rabbit atrium

The method described by Dawes (Brit. J. Pharmacol., 1, 90, 1946) was followed, which consists of electrically stimulating an isolated rabbit atrium with progressive increase in frequency (keeping the other parameters constant) until the atrium no longer manages to follow the rhythm imposed. The $ED_{30}$ in the presence of scalar concentrations of anti-arrhythmic substances was measured.

Rabbit platelet aggregation in vitro

The method of Fregnan (Pharmacology, 7, 115, 1972) was followed. Blood taken from conscious rabbits is centrifuged in the presence of sodium citrate (3.8%) at 350 g. for 10 minutes, so as to separate the plasma rich in platelets (PRP) from the rest. The aggregation of the platelets is carried out by bringing the PRP into contact with adequate doses of sodium adenosine diphosphate in the presence of a possible inhibitor or its carrier. The measurement of aggregation is made continuously by a turbidimetric method. The $ED_{50}$ represents that dose which reduces the aggregation curve by 50%.

Carrageen oedema in the conscious rat

Anti-inflammatory activity was evaluated by the method of Winter and colleagues (Proc. Soc. Exp. Biol., 111, 544, 1962) by endoperitoneally injecting the product under examination one hour before inducing oedema by injecting 0.05 ml. of a 1% suspension of carrageen (intradermally into the plantar portion of a rear paw).

The difference between the volume of the paw determined plethysmographically one hour before and three hours after the carrageen gives a quantitative estimate of the activity of the product tested. Where possible, the $ED_{30}$ was calculated.

Inhibition of spontaneous motility in the mouse

This is evaluated by an actophotometric method, which consists of placing the mice, 30 minutes after oral treatment with the drug or the carrier, in a cage provided with a photoelectric cell counter and counting the number of times the photoelectric cell is passed during a 10 minute stay. It was possible to calculate a $ED_{50}$ with almost all the products examined.

Cataleptic activity in the mouse

This was evaluated by placing the animals, pretreated or otherwise, with their front paws resting on a cork 4.5 cm. high, this position being immediately abandoned by the control animals but maintained for a greater or lesser time depending on the cataleptic activity of the drug under examination. Where possible the $ED_{50}$ was calculated.

Pinching the tail of the mouse

To evaluate the analgesic activity, the method described by Bianchi and colleagues (Brit. J. Pharmacol., 9, 280, 1954) was followed which consists of applying an arterial pincer to the base of the tail in animals treated orally 30 minutes previously with the drug under examination, observing that the control animals react to the pain by squealing.

Antagonism towards a lethal dose of nor-adrenalin in the rat

The animals are treated with a dose of nor-adrenalin (0.5 mg/kg) which is 100% lethal in animals. The activity is calculated by the number of animals protected from death by prior administration of the drug under examination one hour before the agonist. Where possible the $ED_{50}$ was calculated.

Antagonism towards electric shock convulsions in the mouse

This is evaluated by observing the protection given by pretreatment with the drug (30 minutes) against tonic convulsions obtained by applying a 35 volt current to the eyeballs.

Ulcers by constriction in the rat

The method described by Rossi and colleagues (Compt. Rend. Soc. Biol., 150, 2124, 1956) was followed in which the formation of gastric ulcers is induced by immobilising the animal, in a state of fast for 48 hours, in a net for a period of 4 hours.

The protection given by treatment with the drug under examination before the beginning of the constriction period is evaluated by counting both the ulcers and the number of subjects without ulcers.

TABLE

| Compound under test | Acute toxicity $LD_{50}$ mouse mg/kg ip | Spontaneous motility inhibition mouse $ED_{50}$ (*) mg/kg os | Catalectic activity mouse $ED_{50}$ (*) mg/kg os | Systemic analgesic activity, tail pinching in mouse mg/kg os | % |
|---|---|---|---|---|---|
| LR 599 | >1000 | 69.2 | 200.0 | 200 | 30 |
| LR 602 | 125 | 30.0 | | 26 | 30 |
| LR 613 | 300 | 18.0 | 32.4 | 60 | 10 |
| LR 616 | 225 | 40.0 | (40 = 0) | 40 | 0 |
| LR 617 | 100 | 19.6 | | | |
| LR 618 | 250 | 60.0 | 60.0 | 60 | 40 |
| LR 620 | 100 | (26 = 0) | | 26 | 0 |
| LR 628 | 400 | 100.0 | | 100 | 0 |
| LR 630 | 750 | 60.0 | 180.0 | 180 | 0 |
| LR 637 | 1000 | 200.0 | 200.0 | 200 | 30 |
| LR 638 | >1000 | 200.0 | 200.0 | 200 | 10 |
| LR 639 | >1000 | 33.0 | 88.0 | 200 | 0 |
| LR 648 | 125 | (26=20) | | 26 | 0 |
| LR 652 | >1000 | 23.0 | 52.4 | 200 | 0 |
| LR 653 | 420 | 11.6 | 80.0 | 100 | 20 |
| LR 659 | >1000 | | | 200 | 0 |
| LR 660 | >1000 | 100.0 | | 200 | |

| Compound under test | Anti-inflammatory activity carrageenin odedema rat $ED_{30}$ (*) mg/kg ip | α-adrenolytic activity lethal NA rat $ED_{50}$ (*) mg/kg os | Anti-convulsion activity, electric shock, mouse mg/kg os | % att. | Anti-ulcer activity, ulcers by stress in the rat. rats mg/kg ip | Protected in ulcers % | Reduction % |
|---|---|---|---|---|---|---|---|
| LR 599 | (200=20) | 45 | 200 | 0 | 30 | 20 | 48 |
| LR 602 | | (7=0) | 26 | 0 | 10 | 50 | 65 |
| LR 613 | (60=15.2) | (15=20) | 60 | 10 | 30 | 60 | 80 |
| LR 616 | 54 | 5.5 | 40 | 0 | 30 | 10 | 0 |
| LR 617 | | (5=0) | | | 10 | 10 | 17 |
| LR 618 | (60=9.8) | (15=0) | 60 | 10 | 30 | 50 | 71 |
| LR 620 | 36 | 5 | 26 | 20 | 10 | 0 | 0 |
| LR 628 | 35 | 8 | 100 | 0 | 30 | 0 | 0 |
| LR 630 | 145 | 16 | 180 | 10 | 30 | 10 | 0 |
| LR 637 | (200=11.6) | 18 | 200 | 20 | 10 | 57 | 86 |
| LR 638 | (200=14) | (50=0) | 200 | 10 | 10 | 60 | 63 |
| LR 639 | (200=8.1) | 45 | 200 | 0 | 10 | 30 | 28 |
| LR 648 | | (7=0) | 26 | 20 | 10 | 10 | 32 |
| LR 652 | 163 | 13.3 | 200 | 40 | 30 | 50 | 68 |
| LR 653 | (100=25.4) | 12.8 | 100 | 20 | | | |
| LR 659 | | | 200 | 30 | 10 | 50 | 50 |
| LR 660 | | | 200 | 20 | 10 | 50 | 50 |

| Compound under test | Acute toxicity mouse $LD_{50}$ mg/kg ip | Acute toxicity rat $LD_{50}$ mg/kg iv | CaCl$_2$ anaesthetised rat $ED_{50}$ mg/kg iv | I.T.(1) | Electrical stimulation in isolated rabbit atrium $ED_{30}$ mcg/ml | TD mcg/ml | I.T. (2) | Platelet anti-aggregation activity, rabbit in vitro $ED_{50}$ mg/ml |
|---|---|---|---|---|---|---|---|---|
| LR 602 | 125 | 84 | 3.5 | 24 | 10.0 | 300 | 30.0 | 0.80 |
| LR 617 | 100 | 62 | 4.0 | 15 | 4.3 | 300 | 69.0 | 0.80 |
| LR 618 | 250 | 130 | 15.0 | 9 | 35.4 | 300 | 8.5 | 0.65 |
| LR 620 | 100 | 24 | 2.0 | 12 | 1.0 | 30 | 30.0 | 0.65 |

(1) = Therapeutic index obtained from the ratio $LD_{50}$ rate iv/$ED_{50}$
(2) = Therapeutic index obtained from the ratio TD (dose which abolishes the spontaneous contraction of the atrium)/$ED_{30}$
(*) = As the $ED_{30}$ or $ED_{50}$ data are lacking, the quantity of substance in mg/kg and the respective percentage activity are given in parentheses.

The following Examples illustrate the invention. The melting and boiling points are not corrected. The identity of the substances and their purity have been ascertained by elementary analysis of carbon, hydrogen and nitrogen (and halogens where present), infrared, N.M.R. and U.V. spectra.

EXAMPLE 1

4-p-fluorophenyl-5-β-[4'-hydroxy-4'-(p-chlorophenyl)-piperidino]ethyl-4-thiazolin-2-one hydrochloride A mixture of 10 g of 4-p-fluorophenyl-5-β-chloroethyl-4-thiazolin-2-one, 16.4 g of 4-hydroxy-4-(p-chlorophenyl)-piperidine, and a catalytic quantity of KI in 200 cc of toluene is heated in a closed tube for 35 hours. The solid present is filtered off and the filtrate is shaken with a 1:1 solution of HCl. A solid precipitates and is dissolved in acetone and recrystallised. M.P. = 192° C (from alcohol).

The following are prepared in like manner:
4-p-fluorophenyl-5-β-(N'-phenylpiperazino)ethyl-4-thiazolin-2-one M.P. = 192° C (from alcohol)
4-p-fluorophenyl-5-β-morpholinoethyl-4-thiazolin-2-one hydrochloride M.P. = 262° C (from alcohol)
4-p-fluorophenyl-5-β-piperidinoethyl-4-thiazolin-2one hydrochloride M.P. = 272° C (from alcohol)
4-p-fluorophenyl-5-β-diethylaminoethyl-4-thiazolin-2-one M.P. = 91° C (from hexane)
4-p-fluorophenyl-5-β-(N-methylphenylethylamino)ethyl-4-thiazolin-2-one maleate M.P. = 179° C (from alcohol)
4-phenyl-5-β-(N-methylphenylethylamino)-ethyl-4-thiazolin-2-one maleate M.P. = 161° C (from alcohol)
4-p-chlorophenyl-5-β-(N-methylphenylethylamino)-ethyl-4-thiazolin-2-one maleate M.P. = 164° C (from alcohol)
4-p-methoxyphenyl-5-β-(N-methylphenylethylamino)-ethyl-4-thiazolin-2-one maleate M.P. = 171° C (from alcohol)
4-phenyl-5-β-(N'-phenylpiperazino)-ethyl-4-thiazolin-2-one M.P. = 199° C (from alcohol)
4-p-chlorophenyl-5-β-(N'-phenylpiperazino)-ethyl-4-thiazolin-2-one M.P. = 230° C (from alcohol)
4-p-methoxyphenyl-5-β-(N'-phenylpiperazino)-ethyl-4-thiazolin-2-one M.P. = 210° C (from alcohol)
4-p-fluorophenyl-5-β-[7,12-dioxa-3-azaspiro[5.6]-dodec-3-yl]-ethyl-4-thiazolin-2-one hydrochloride M.P. = 205° C (from alcohol)
4-p-fluorophenyl-5-β-(4'-benzoylaminopiperidino)-ethyl-4-thiazolin-2-one M.P. = 213° C (from alcohol)
4-p-fluorophenyl-5-β-(N'-o-methoxyphenyl-piperazino)-ethyl-4-thiazolin-2-one M.P. = 181° C (from alcohol)
4-phenyl-5-β-dimethylaminoethyl-4-thiazolin-2-one M.P. = 115° C (from hexane)

The 4-p-fluorophenyl-5-β-chloroethyl-4-thiazolin-2-one is prepared in the following manner: A mixture of 30 g of 1-p-fluorobenzoyl-1-bromo-3-chloropropane (prepared in accordance with our Italian Patent Application No. 23444 A/72 filed 22.4.1972), 11.5 g of potassium thiocyanate, 120 cc of ethanol and 6 cc of water is boiled under reflux for 4 hours. The precipitated solid is filtered while hot and 1-p-fluorobenzoyl-1-thiocyano-3-chloropropane precipitates from the filtrate on cooling. 22.1 g of the latter, 66 cc of glacial acetic acid and 11 cc of concentrated H$_2$SO$_4$ are boiled under relux for 4 hours. The acetic acid is removed from the reacting mass under reduced pressure and the residue is extracted while hot with chloroform. The chloroform solution is evaporated to dryness under reduced pressure and the residue recrystallised. M.P. = 138° C (from isopropyl alcohol).

The following are prepared in like manner: 4-phenyl-5-β-chloroethyl-4-thiazolin-2-one, M.P. = 129° C (from isopropyl alcohol)
4-p-chlorophenyl-5-β-chloroethyl-4-thiazolin-2-one, M.P. = 176° C (from isopropyl alcohol)
4-p-methoxyphenyl-5-β-chloroethyl-4-thiazolin-2-one, M.P. = 133° C (from isopropyl alcohol).

The aforesaid preparation of 1-p-fluorobenzoyl-1-bromo-3-chloropropane is carried out by reacting 1-p-fluorobenzoyl-3-chloropropane with bromine in acetic acid, as indicated in EXAMPLE 6 of Italian Patent Application No. 23444.

EXAMPLE 2

3-methyl-4-p-fluorophenyl-5-β-(N'-phenylpiperazino)-ethyl-4-thiazolin-2-one

A solution of 0.69 g of sodium in 80 cc of absolute methanol is added to a suspension of 11.5 g of 4-p-fluorophenyl-5-β-(N'-phenylpiperazino)ethyl-4-thiazolin-2-one in 150 cc of absolute methanol. It is slightly heated for 15 minutes and 14 g of methyl iodide are added. The solution is heated under reflux for 2 hours and then evaporated to dryness under vacuum. The residue is redissolved in hot benzene and filtered and the filtrate is evaporated to dryness under vacuum. M.P. = 130°–132° C (from alcohol).

The following is prepared in a like manner: 3-methyl-4-p-fluorophenyl-5-β-[(4'-hydroxy-4'-p-chloro phenyl)-piperidino]-ethyl-4-thiazolin-2-one, M.P. = 137° C (from isopropyl alcohol).

EXAMPLE 3

3-methyl-4-phenyl-5-β-(N-methyl-phenylethylamino)ethyl-4-thiazolin-2-one oxalate A solution of 6 g of 3-methyl-4-phenyl-5-β-chlorethyl-4-thiazolin-2-one, 6.4 g of N-methylphenylethylamine, and a catalytic quantity of KI in 150 cc of toluene is heated under reflux for 35 hours. It is filtered and the filtrate is shaken with dilute HCl. The aqueous phase is made alkaline with ammonia and extracted with chloroform. It is dried over Na$_2$SO$_4$ and evaporated with chloroform. It is dried over Na$_2$SO$_4$ and evaporated to dryness. The residue is transformed into the corresponding oxalate. M.P. = 187° C (from alcohol).

The following are prepared in like manner:
3-methyl-4-p-fluorophenyl-5-β-phenylethylamino-ethyl-4-thiazolin-2-one maleate. M.P. = 178° C (from isopropyl alcohol)
3-methyl-4-p-fluorphenyl-5-β-(3', 4'-dimethoxy-phenylethylamino)-ethyl-4-thiazolin-2-one hydrochloride, M.P. = 169° C (from alcohol).

The 3-methyl-4-phenyl-5-β-chloroethyl-4-thiazolin-2-one is prepared in the following manner. A solution of 21.9 g of 1-benzoyl-1-bromo-3-chloropropane and 5 g of ethyl N-methyl-thiocarbamate in 50 cc of dioxan is heated under reflux for 10 hours, and then evaporated to dryness under reduced pressure, M.P. = 88°-90° C (from hexane).

The following is prepared in a like manner:
3-methyl-4-p-fluorophenyl-5-β-chloroethyl-4-thiazolin-2-one, M.P. = 89° C (from hexane).

EXAMPLE 4

3-acetyl-4-p-fluorophenyl-5-β-(N'-phenyl-piperazino)ethyl-4-thiazolin-2-one 21.4 g of acetic anhydride are added to a solution of 8.2 g of 4-p-fluorophenyl-5-β-(N'-phenyl-piperazino)ethyl-4-thiazolin-2-one in 40 cc of anhydrous pyridine. It is heated under reflux for 20 hours, and then evaporated to dryness under reduced pressure and the residue is heated with hexane and filtered. The filtrate is evaporated to dryness, M.P. = 103° C (from alcohol).

In a like manner the following is prepared:

3-acetyl-4-p-fluorophenyl-5-β-(N'-o-methoxyphenyl-piperazino)-ethyl-4-thiazolin-2-one, M.P. = 99° C (from alcohol).

EXAMPLE 5

3-methyl-4-phenyl-5-β-(3',4'-dimethoxyphenylethylamino)-ethyl-4-thiazoline-2-thione hydrochloride A solution of 3 g of 3-methyl-4-phenyl-5-β-chloroethyl-4-thiazoline-2-thione, 4.05 g of 3,4-dimethoxyphenylethylamine and a catalytic quantity of KI in 50 cc of toluene is heated under reflux for 66 hours. The solid present is filtered off and the filtrate is shaken with dilute HCl. The separated aqueous phase is made alkaline with ammonia and shaken with chloroform. The separated organic phase is dried over $Na_2SO_4$ and evaporated to dryness. The hydrochloride is produced from the residue with alocholic HCl. M.P. = 221° C (from alcohol).

The following are prepared in a like manner:

3-methyl-4-phenyl-5-β-phenylethylaminoethyl-4-thaizoline-2-thione oxalate M.P. = 228° C (from alcohol)

3-methyl-4-phenyl-5-β-(N-methylphenylethylamino)-ethyl-4-thiazoline-2-thione M.P. = 73°–6° C (from hexane)

3-methyl-4-phenyl-5-β-phenoxyisopropylaminoethyl-4-thiazoline-2-thione maleate M.P. = 179° C (from alcohol)

3-methyl-4-phenyl-5-β-isopropylaminoethyl-4-thiazoline-2-thione maleate M.P. = 228° C (from alcohol)

3-methyl-4-p-fluorophenyl-5-β-diethylaminoethyl-4-thiazoline-2-thione hydrochloride M.P. = 160° C (from isopropyl alcohol)

3-methyl-4-p-fluorophenyl-5-β-(N-methylphenylethylamino)-ethyl-4-thiazoline-2-thione hydrochloride M.P. = 195° C (from isopropyl alcohol)

3-methyl-4-p-fluorophenyl-5-β-(N'-phenyl-piperazino)-ethyl-4-thiazoline-2-thione hydrochloride M.P. = 270° C (from alochol).

The 3-methyl-4-phenyl-5-β-chloroethyl-4-thiazoline-2-thione is prepared in the following manner: A solution of 33 g of 1-benzoyl-1-bromo-3-chloropropane in 150 cc of absolute alcohol is added slowly to a suspension of 20 g of methyl ammonium N-methyldithiocarbamate in 150 cc of absolute alcohol. The mixture is agitated for 2 hours at ambient temperature and the solvent is then evaporated under reduced pressure. The residue is redissolved in chloroform, washed with water and the separated organic phase is dried over $Na_2SO_4$ and then evaporated to dryness.

The residue is heated under reflux for 2 hours with 200 cc of 20% HCl. The solid present is filtered off. M.P. = 116° C (from alcohol).

The following is prepared in a like manner:

3-methyl-4-p-fluorophenyl-5-β-chloroethyl-4-thiazoline-2-thione, M.P. = 105° C (from alcohol).

The 4-p-fluorophenyl-5-β-chloroethyl-4-thiazoline-2-thione is prepared likewise, using the ammonium dithiocarbamate and omitting hot treatment with HCl. M.P. = 176° C (from alcohol).

EXAMPLE 6

4-p-chlorophenyl-5-(N'-phenylpiperazino)methyl-4-thiazolin-2-one

A mixture of 15 g of 4-p-chlorophenyl-4-thiazolin-2-one, 2.12 g of paraformaldehyde, 11.5 g of phenylpiperazine, and 3.42 g of anhydrous $ZnCl_2$ in 600 cc of absolute methanol is heated under reflux for 4 hours. The solvent is evaporated under reduced pressure and the residue dissolved in chloroform and shaken with a 20% HCl solution.

The hydrochloride phase is made alkaline with ammonia and shaken with chloroform. The organic phase is dried over $Na_2SO_4$ and evaporated under vacuum. M.P. = 194° C (from alcohol).

The following are prepared in a like manner:

4-p-chlorophenyl-5-piperidinomethyl-4-thiazolin-2-one M.P. = 183° C (from alcohol)

4-p-chlorophenyl-5-(N-methylphenylethylamino)-methyl-4-thiazolin-2-one M.P. = 130° C (from alcohol)

4-p-chlorophenyl-5-morpholinomethyl-4-thiazolin-2-one M.P. = 189° C (from alcohol).

The 4-p-chlorophenyl-4-thiazolin-2-one is prepared in the following manner: A solution of 150 g of p-chloro-ω-bromo-acetophenone, 69 g of potassium thiocyanate in 500 cc of alcohol and 36 cc of distilled water is heated under reflux for 30 minutes. The solid present is filtered off and after drying, it is heated under reflux for 3 hours in a solution of 470 cc of acetic acid and 80 cc of $H_2SO_4$. The solvent is removed under vacuum. The residue has M.P. = 206° C (from alcohol).

EXAMPLE 7

3-methylaminocarbonyl-4-p-fluorophenyl-5-β-(N'-o-methoxyphenylpiperazino)ethyl-4-thiazolin-2-one hydrochloride A mixture of 0.5 g of 4-p-fluorophenyl-5-β-(N'-o-methoxyphenylpiperazino)ethyl-4-thiazolin-2-one and 0.45 g of methylisocyanate are heated in a closed tube for 4 hours. Alcoholic HCl is added to the reaction mass. The residue has M.P. = 193° C (from isopropyl alcohol).

EXAMPLE 8

3-benzoyl-4-p-fluorophenyl-5-β-(N'-o-methoxyphenyl-piperazino)ethyl-4-thiazolin-2-one hydrocloride A mixture of 0.5 g of 4-p-fluorophenyl-5-β-(N'-o-methoxyphenylpiperazino)ethyl-4-thiazolin-2-one and 0.85 cc of benzoyl chloride in 5 cc of pyridine is heated under reflux for 12 hours. It is evaporated to dryness under vacuum. The residue has M.P. = 240° C (from alcohol).

EXAMPLE 9

Cu (II) complex of 4-phenyl-5-β-dimethylaminoethyl-4-thiazolin-2-one hydrochloride 0.2 cc of an aqueous alcoholic solution of $CuCl_2$ is added to a solution of 0.2 g of 4-phenyl-5-β-dimethylaminoethyl-4-thiazolin-2-one in 1 cc of alcohol and 0.2 cc of water. The complex formed has M.P. = 205° C (from alcohol).

The following are prepared in a like manner:

Cu (II) complex of 4-p-fluorophenyl-5-β-morpholinoethyl-4-thiazolin-2-one hydrochloride, M.P. = 167° C (from alcohol)

Cu (II) complex of 3-methyl-4-p-fluorophenyl-β-(N'-phenylpiperazino)ethyl-4-thiazolin-2-one hydrochloride, M.P. = 160° C (from alcohol)

Cu (II) complex of 4-p-chlorophenyl-5-(N'-phenyl-piperazino)-methyl-4-thiazolin-2-one hydrochloride, M.P. = 181° C (from alcohol).

We claim:

1. 4-Aryl-5-aminoalkyl-4-thiazoline-2-ones of the formula:

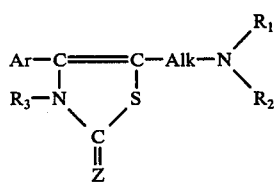

and their pharmaceutically acceptable salts, in which Ar represents phenyl, lower alkylphenyl, trifluoromethylphenyl, lower alkoxyphenyl, lower dialkylaminophenyl, halogen phenyl or lower alkylmercaptophenyl; Alk represents a saturated or unsaturated, linear or branched chain of 1 to 3 carbon atoms;

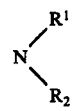

is a piperazine-4 subsituted by phenyl; Z represents an oxygen or sulfur atom; and $R_3$ represents a hydrogen atom or methyl, acetyl, benzoyl or methylaminocarbonyl.

2. A compound of claim 1, wherein Ar is phenyl, p-fluorophenyl, p-chlorophenyl or p-methoxyphenyl; Alk is $CH_2$ or $CH_2CH_2$; $NR_1R_2$ is N'-phenylpiperazino; Z is oxygen; and $R_3$ is hydrogen, methyl or acetyl.

3. A compound according to claim 1 which is 4-p-fluorophenyl-5-β-(N'-phenylpiperazino)ethyl-4-thiazolin-2-one, and its pharmaceutically acceptable salts.

4. A compound according to claim 1 which is 4-phenyl-5-β-(N'-phenylpiperazino)ethyl-4-thiazolin-2-one, and its pharmaceutically acceptable salts.

5. A compound according to claim 1 which is 4-p-chlorophenyl-5-β-(N'-phenylpiperazino)ethyl-4-thiazolin-2-one, and its pharmaceutically acceptable salts.

6. A compound according to claim 1 which is 4-p-methoxyphenyl-5-β-(N'-phenylpiperazino)ethyl-4-thiazolin-2-one, and its pharmaceutically acceptable salts.

7. A compound according to claim 1 which is 3-methyl-4-p-fluorophenyl-5-β-(N'-phenylpiperazino)ethyl-4-thiazolin-2-one, and its pharmaceutically acceptable salts.

8. A compound according to claim 1 which is 4-p-chlorophenyl-5-(N'-phenylpiperazino)methyl-4-thiazolin-2-one, and its pharmaceutically acceptable salts.

9. A compound according to claim 1, which is 3-methyl-4-p-fluorophenyl-5-β-(N'-phenyl-piperazino)ethyl-4-thiazoline-2-thione, and its pharmaceutically acceptable salts.

* * * * *